United States Patent [19]

Schweighardt

[11] Patent Number: 4,603,115

[45] Date of Patent: Jul. 29, 1986

[54] AUTOMATED PROCESS FOR SOLVENT SEPARATION OF ORGANIC/INORGANIC SUBSTANCE

[75] Inventor: Frank K. Schweighardt, Upper Macungie, Pa.

[73] Assignee: International Coal Refining Company, Allentown, Pa.

[21] Appl. No.: 662,911

[22] Filed: Oct. 19, 1984

Related U.S. Application Data

[63] Continuation-in-part of Ser. No. 458,373, Jan. 17, 1983, Pat. No. 4,492,674.

[51] Int. Cl.⁴ .............................................. G01N 1/18
[52] U.S. Cl. ................................... 436/178; 210/651; 210/739; 436/139; 422/281
[58] Field of Search ..................... 436/50, 139, 178; 422/62, 101; 435/803, 804, 814, 816, 820; 210/650, 651, 748, 739; 208/8 LE; 196/14.52; 364/500

[56] References Cited

U.S. PATENT DOCUMENTS

| | | | |
|---|---|---|---|
| 4,219,530 | 8/1980 | Kopp et al. | 422/69 |
| 4,252,769 | 2/1981 | Hood et al. | 422/50 |
| 4,311,586 | 1/1982 | Baldwin et al. | 210/101 |

FOREIGN PATENT DOCUMENTS

| | | | |
|---|---|---|---|
| 1189554 | 10/1959 | France | 422/261 |
| 821939 | 9/1959 | United Kingdom | 422/128 |

OTHER PUBLICATIONS

Solvent Extraction of Coal Derived Products, Schweighardt et al., Analytical Chemistry, vol. 50, No. 9, Aug. 1978, pp. 1381–1382.

*Primary Examiner*—David L. Lacey

[57] ABSTRACT

There is described an automated process for the solvent separation of organic/inorganic substances that operates continuously and unattended and eliminates potential errors resulting from subjectivity and the aging of the sample during analysis. In the process, metered amounts of one or more solvents are passed sequentially through a filter containing the sample under the direction of a microprocessor control apparatus. The mixture in the filter is agitated by ultrasonic cavitation for a timed period and the filtrate is collected. The filtrate of each solvent extraction is collected individually and the residue on the filter element is collected to complete the extraction process.

21 Claims, 4 Drawing Figures

AUTOMATED PROCESS FOR SOLVENT SEPARATION OF ORGANIC/INORGANIC SUBSTANCE

The Government of the United States of America has rights in this invention pursuant to Contract No. DE-AC05-78OR03054 (as modified) awarded by the U.S. Department of Energy.

CROSS-RELATED APPLICATION

This application is a continuation-in-part of Ser. No. 458,373 filed Jan. 17, 1983, now U.S. Pat. No. 4,492,674 and all of the teachings therein are here incorporated by reference.

BACKGROUND OF THE INVENTION

This invention relates generally to an automated process and apparatus for the solvent separation of organic-/inorganic substances. More particularly, the invention relates to an automated process and apparatus for the solvent extraction of molecular constituents of coal-derived material such as coal liquefaction process streams.

In processes such as the SRC-I process for the solvent refining of coal there is a need for the separation and characterization of coal-derived oils. While many procedures have been used over the past forty years to monitor coal conversion products, no standard procedure has evolved that is widely used to separate and characterize liquefied or solvent refined coal products. The problems with the prior procedures are that they lack reproducibility, give low or high material balance, are time consuming, and/or involve frequent subjective judgments.

The state of the prior art is described in the following prior art materials, which pertains to manual procedures, whereas the process and apparatus of this invention are automated.

ANALYTICAL CHEMISTRY, Volume 50, No. 9, August, 1978, page 1381+, Article Entitled "Solvent Extraction of Coal-Derived Products,"

WILSONVILLE, ALABAMA ANALYTICAL PROCEDURES, 34550-3, "Determination of Product Distribution by Soxhlet Extraction" and 34550-17, "Benzene Insolubles in Filtrate."

FUEL, Volume 58, July, 1979, pages 539–541, Article by Burke et al. Entitled "Liquid Column Fractionation; A Method of Solvent Fractionation of Coal Liquefaction and Petroleum Products."

SUMMARY OF THE INVENTION

It is the general object of the invention to provide an automated process and apparatus for the solvent separation of organic/inorganic substances that operates continuously and unattended and eliminates potential errors resulting from subjectivity and the aging of the sample during analysis.

Briefly stated, the process and apparatus of the invention comprise a procedure wherein a weighed amount of organic/inorganic material is delivered into a filter and metered amounts of a series of solvents or solvent mixtures are passed sequentially through the filter under the direction and control of a micro-processor. For purposes of this invention, the term "solvent mixture" means one or more solvents (e.g., three or more virgin solvents) or a mixture of a single solvent with the same or different solute/solvent concentration. The mixture in the filter is agitated by means of ultrasonic cavitation for a timed period and the filtrate is collected. The completion of the extraction by each solvent is determined by a spectrophotometric response whereupon the next solvent in the series is metered into the filter. The filtrates of each solvent extraction are collected individually and the residue from the filter element is collected to complete the extraction process.

In the automated process of the invention the extraction endpoint is determined objectively at room temperature under inert gas conditions and all the sequential steps are controlled by means of a microprocessor which selects the next step and number of times each step is repeated to attain an endpoint. The endpoint is reached when the response reaches a pre-set value on the spectrophotometer.

The automated process and apparatus of the invention solves the problem of subjectivity in solvent extraction to determine endpoints. Moreover, it performs the unattended, complete extraction of coal liquids at room (ambient) temperatures under an inert atmosphere. This unique approach also solves the problem of sample aging and operator dependent results.

A feature of the invention is the provision of a continuous automated operation to achieve in one apparatus a plurality of solvent extractions.

Another feature of the invention is the use of ultrasonic energy to enhance extraction and mix the organic-/inorganic material in the filter.

An added feature of the invention is the use of a spectrophotometric device to determine the endpoint of solvent extraction.

Another feature of the invention is the use of inert gas under room temperature to complete the analysis.

The value of the automated apparatus and process of the invention is demonstrated by the substantial reduction in the man-hours required to perform the separation of the coal-derived oils of the type used in the SRC-I process. At the SRC-I pilot plant at Wilsonville, Ala. a manual separation process involving Soxhlet extraction and precipitation is used and takes approximately 34 man-hours to complete. Moreover, a manual procedure of a type similar to that of the invention which utilizes sequential ultrafiltration requires about 15–20 man-hours to perform. By way of marked contrast, the automated process in accordance with the invention can be performed in less than four man-hours.

DETAILED DESCRIPTION OF THE PREFERRED EMBODIMENT

Figure 1:
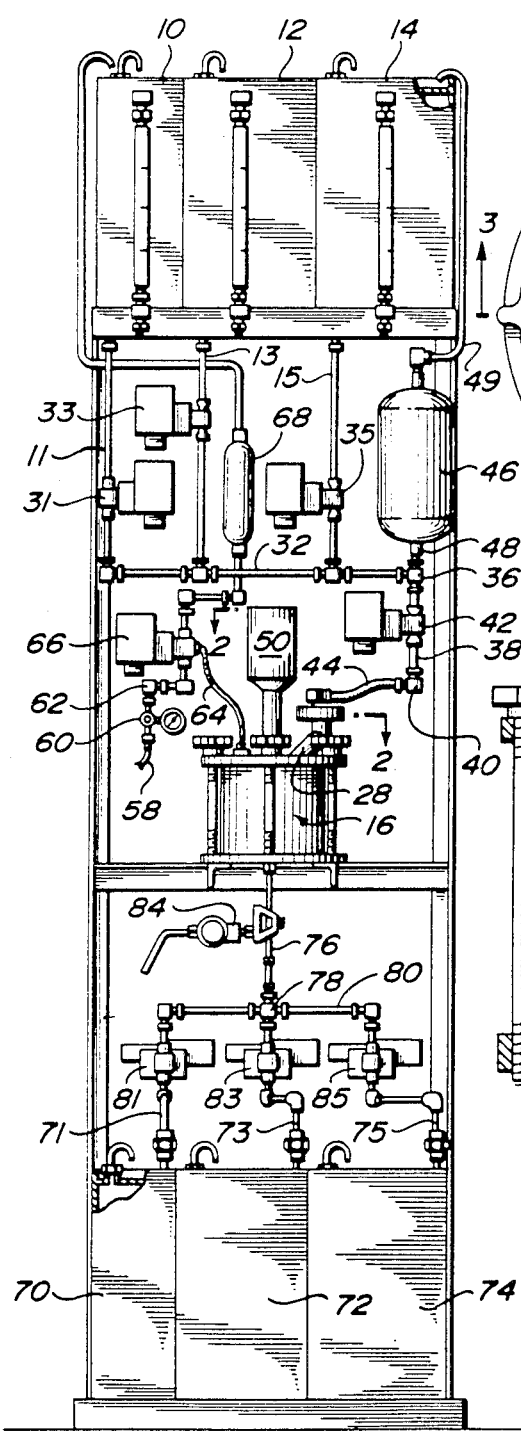
FIG. 1 is a front elevation of a preferred embodiment of the apparatus in accordance with the invention.

While the preferred embodiment of the invention shown in the drawings and to be described hereafter is particularly adapted for the solvent extraction of pentane soluble, benzene soluble and pyridine soluble constituents of a coal-derived material, it will be apparent that the invention is more broadly applicable to analytical procedures for the handling of various types of samples. For example, the invention is applicable to various natural product extraction procedures such as shale and petroleum products, and to various pharmaceutical and toxicological applications. The process of this invention provides a unique approach to the purification, extraction and ultrafiltration of fossil fuels, vegetable matter and animal matter plus various rock and minerals. Petroleum crudes such as atmospheric and vacuum tower distillation bottoms can be slurried with a non-polar $C_5$ to $C_{10}$ alkane solvent, sonicated and extracted to an endpoint defined by a detector, i.e. ultraviolet, infrared, refractive index, etc. Oil shale contemplated within this invention include retort or solvent extracted total product, atmospheric distillation bottoms and vacuum tower distillation bottoms hile suitable tar sands are exemplified by solvent extracted or thermally induced oil concentrates, atmospheric distillation bottoms and vacuum distillation bottoms.

Leaves, bark, roots, stems, wood, seeds, nuts, petals and fruit in a fresh, dried or chipped state can be separated via this process. For example, a chosen material from this list of once living entities is situated in the filter portion of the apparatus, covered with solvent and sonicated resulting in ultimate filtration. Organic polymers, organic-inorganic co-polymers and inorganic polymers in addition to animal cell tissue, bacteria and tissue cultures may also be separated via the unique process.

Moreover, the capability of the apparatus and the automated process could be adapted to analogous analytical procedures involving multiple solvent extractions of a multitude of materials, utilizing a broad spectrum of solvents having different solvent properties, but employing the novel features of the invention. For the purpose of the present invention, it is understood that solvent properties include, but are not limited to, polarity, ionic strength, dipole moment, pH, density and viscosity.

The apparatus of the invention shown in the drawings comprises means providing a supply of three virgin solvents arranged in order of increasing polarity. Such means comprises three virgin liquid reservoirs 10, 12 and 14 containing supplies of the solvents n-pentane, benzene and pyridine, respectively. The reservoirs 10, 12 and 14 are mounted at the top of the apparatus as is shown in FIG. 1 so as to provide a gravity feed as will be described hereafter. It should be noted at this point that the gravity feed will eliminate the need for a vacuum system which produces a large difference in the solubility parameters of various contemplated separations.

Figure 3:
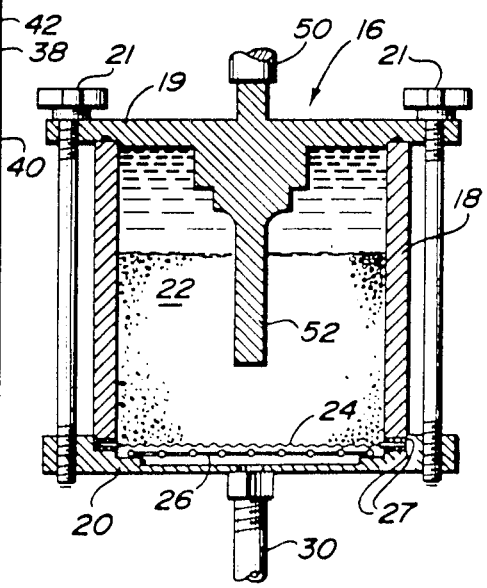
FIG. 3 is a sectional view taken on line 3—3 of FIG. 2.

A filter 16 is mounted beneath the reservoirs 10, 12 and 14 and is of a type capable of performing absolute filtration separation of solids from liquids by pressure filtration. All contact surfaces of filter 16 are Teflon-coated and the filter is preferably made of stainless steel and provided with Teflon O-ring seals. A suitable filter which may be modified for use in the apparatus of the invention is the 316 Stainless Steel Hazardous Waste Filtration Device manufactured by the Millipore Corporation. Filter 16 comprises a hollow cylindrical body 18 located between a top inlet plate 19 and a bottom outlet plate 20, which parts are assembled together by four clamping means 21 as shown in FIG. 3. The internal surfaces of body 18 and plates 19 and 20 define a cylindrical filter chamber 22 having a filter element 24 located at the bottom thereof and resting on a Teflon-faced underdrain support 26. The perimeter of filter element 24 is held between a pair of Teflon O-rings 27.

The pore size of filter element 24 may vary with the particular sample being tested, a preferred range being from 0.5 to 10.0 microns. The process of this invention operates in a unique manner and functions very different from the prior art. The extraction achieved in this process occurs because the sonicator disrupts or fractures aggregate particles and by its localized heating causes an increase in the extract solubility in the solvent. The particles lie on the fine filter element 24 that has a preferred pore size of 0.5 to 10 $\mu$ to produce a filtrate that is $>0.5$ $\mu$ solids free.

Figure 2:
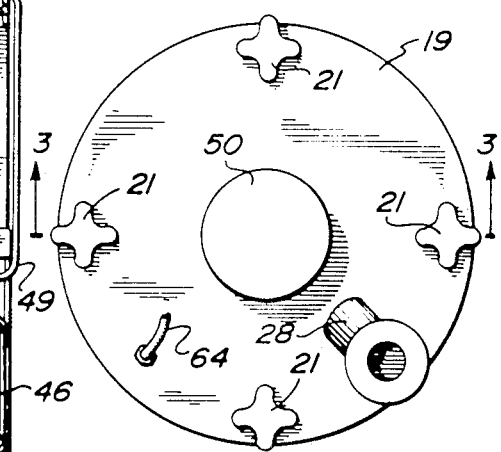
FIG. 2 is a sectional view taken on line 2—2 of FIG. 1.

Filter 16 is provided with a fill tube 28 mounted on inlet plate 19 and providing a passage through which either the sample or the solvent can be delivered into filter chamber 22. As is shown in FIG. 2, fill tube 28 is offset from the center of inlet plate 19. Filter 16 is provided with an outlet tube 30 from which the filtered liquid is discharged from the filter chamber 22 after passing through the filter element 24.

As will be apparent to one skilled in the art, various pore sizes and types of the filter element 24 may be utilized. The essential requirement of the filter element is that it be compatible with the physical and chemical properties of the product and solvents being filtered.

Means are provided for delivering individual solvent streams from the virgin supply reservoirs 10, 12 and 14 to the filter chamber 22. Such means comprises three vertically extending flow lines 11, 13 and 15 extending from receivers 10, 12 and 14, respectively, to a horizontally extending flow line 32. Flow lines 11, 13 and 15 are provided with control valves 31, 33 and 35, respectively, for controlling the flow therethrough. The downstream end of flow line 32 is connected to the center connection of a T-shaped fitting 36. A flow line 38 extends downwardly from fitting 36 and has its downstream end connected to an L-shaped fitting 40. Flow line 38 is provided with a flow control valve 42 for controlling the flow therethrough. A flexible tube 44 is connected between fitting 40 and the fill tube 28 for delivering flow therebetween.

Means are provided for metering the amount of the individual solvent streams delivered to the filter 16. To this end, a receiver 46, in the form of a double ended sample cylinder, e.g., a Whitey flask, is mounted above fitting 36 and has its lower end in flow communication therewith through a short flow tube 48. The upper end of receiver 46 is provided with an overflow and vent line indicated at 49. Receiver 46 is of a size to contain one liter of solvent.

As will be described more fully hereafter, the above described parts can be utilized to deliver solvent from any one of the reservoirs 10, 12 or 14 through the inlet tube 28 into filter chamber 22. Moreover, it will be apparent that by the proper sequencing of the valves 31, 33, 35 and 42 metered charges of one liter of virgin solvent may be delivered at a time.

The apparatus of the invention is provided with means for ultrasonically agitating the contents of filter chamber 22. Such means comprises an ultrasonic transducer or sonicator 50, which is mounted on the top of inlet plate 19 with its probe 52 extending through inlet plant 19 into the interior of filter chamber 22 as shown in FIG. 3. Sonicator 50 functions to ultrasonically agitate to enhance the extraction of the contents of filter chamber 22 to reduce the filtering time.

Means are provided for supplying an inert gas, namely nitrogen, under pressure and at ambient conditions to filter chamber 22. The supply gas pressure is sufficient to cause the flow of the solvent through filter element 24 during a filtering operation. The inert gas is supplied from a suitable source through a hose line 58, a pressure regulator 60 and a supply line 62 connected to a flexible inlet hose 64 connected to an inlet port in the inlet plate 19. A flow control valve 66 is located in the inert gas supply line between supply line 62 and flexible hose 64 for controlling the flow of inert gas as determined by the control means for the apparatus.

The inert gas supply is provided with a vent and trap means comprising a double ended sample cylinder 68, e.g., Whitey flask, connected to the inert gas supply line upstream of control valve 66 as shown in FIG. 1.

Control of solvent selection is made by setting microprocessor 99 for a preselected drain-time. The drain-time may be any time value from 0-999 minutes. In common practice, four minutes drain-time provides sufficient time for filter 16 to drain of any solvent. Subsequent selection of the next extraction solvent is made by entering into the microprocessor 99 the total number of cycles that each solvent is to pass through filter 16. For example, in common practice six cycles are used for each solvent extraction.

It should be understood, that in accordance with this invention, other techniques and apparatus could be employed to control solvent selection, including but not limited to back-pressure sensing devices, a level indicator or the like.

At the bottom of the apparatus there are provided three liquid receivers 70, 72 and 74 for receiving the solution flowing from the outlet of filter 16. The receivers 70, 72 and 74 serve as containers for the solvent and the sample materials dissolved therein and are associated, respectively, with the three solvent containers 10, 12 and 14 for receiving the solvent passing therefrom. The arrangement serves to segregate individual solvent extraction streams.

Flow lines are provided for delivering the solution passing from filter 16 to receivers 70, 72 and 74 in individual streams. Such means comprises a vertical discharge flow line 76 passing from outlet tube 30 of filter 16 to a fitting 78 connected in a horizontally extending distribution flow line 80 located above the three solvent receivers 70, 72 and 74. Three vertically extending flow lines 71, 73 and 75 pass from the flow line 80 to the three solvent receivers 70, 72 and 74, respectively, as shown in FIG. 1. Flow lines 71, 73 and 75 are provided with flow control valves 81, 83 and 85, respectively, for controlling the flow therethrough in a manner to be described hereafter.

Figure 4:
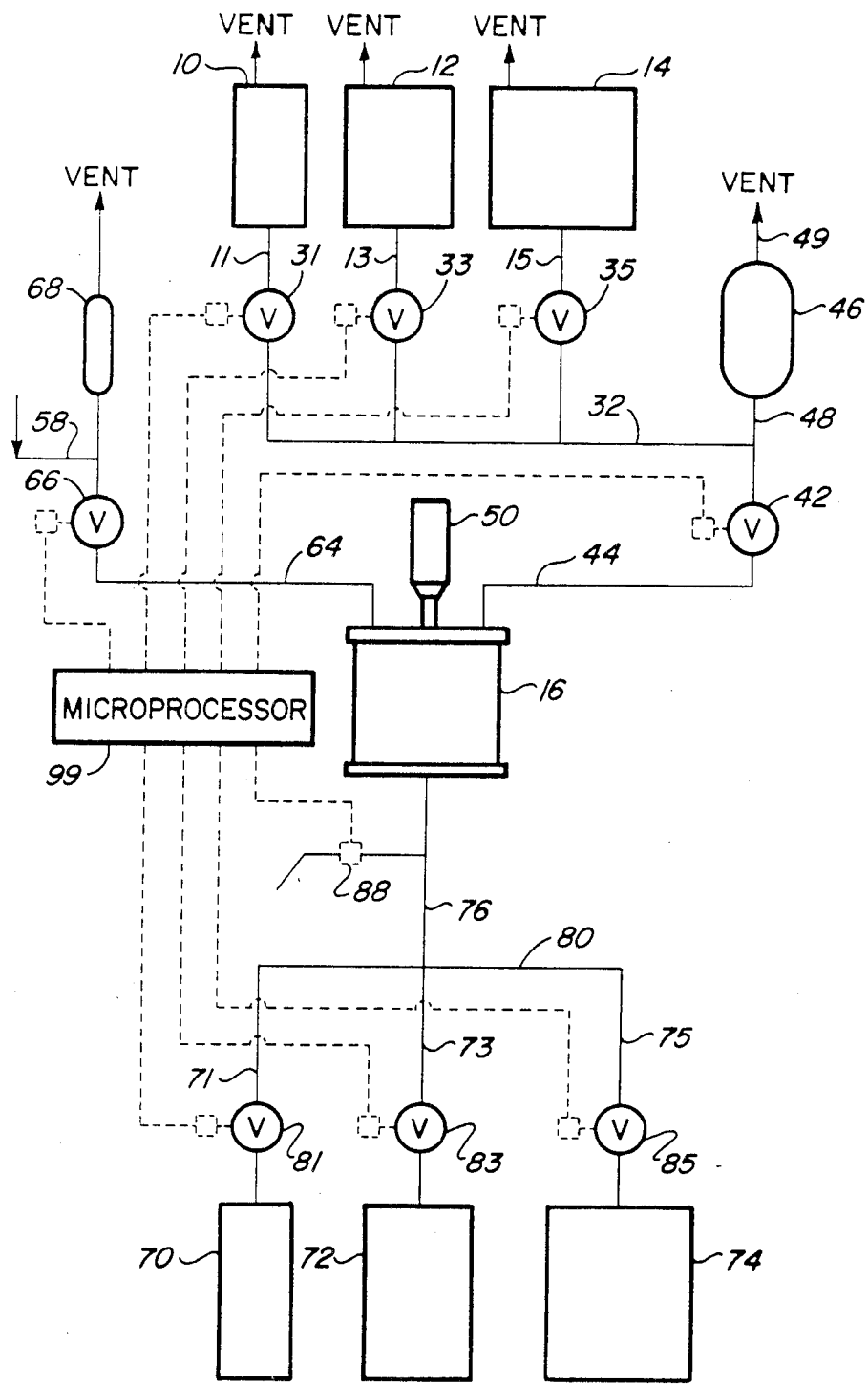
FIG. 4 is a schematic view of the process of the invention showing the control means therefor.

Means are provided for sensing the endpoint of the individual solvent extractions, such means determining the condition of the solution flowing from filter chamber 22 to a solvent receiver 70, 72 or 74 and providing a signal indicative of the endpoint of the solvent extraction. In the preferred embodiment shown in FIG. 1, the endpoint sensing means comprises an ultraviolet detector 88 that has a feedback loop and senses a spectrophotometric response that matches that loop. The detector operates to send a signal when the endpoint of the solvent extraction has been reached. The operation of the endpoint detector will be described more fully in connection with the description of the operation of the apparatus. As shown in FIG. 4 the endpoint detector is located to sense the flow of the filtered solution passing through line 76 between filter 16 and the distributing line 80. The completion of the extraction procedure by each solvent is determined by detector 88 comparing a spectrophotometric response resulting from sensing the condition of the solvent stream passing through line 76 with a reference indicative of a condition equivalent to solvent only. Thus, when detector 88 determines that there is nothing but solvent in the solvent stream passing through line 76, it puts out a signal to microprocessor control means 99 so that the apparatus will sequence to the next solvent extraction step.

The apparatus of the invention is provided with control means for sequentially operating the flow control valves 31, 33, 35, 42, 66, 81, 83 and 85 described above for performing sequential solvent extraction by the solvents in reservoirs 10, 12 and 14. The control means is shown schematically in FIG. 4 and is comprised of conventional microprocessor elements which are arranged to control the operation of the eight flow control valves in a sequence for achieving the sequential solvent extraction in accordance with the method of the invention.

Flow control valves 31, 33, 35, 42, 66, 81, 83 and 85 are pneumatic-operated, ($N_2$ or air), explosion proof valves and have their control mechanisms constructed and arranged to be actuated by control signals from the microprocessor control as shown in FIG. 4. Also, microprocessor 99 is connected to detector 88 for receiving a signal to sequence the apparatus to the next solvent extraction step.

The various elements of the microprocessor control shown in FIG. 4 are conventional and the manner in which the connections are made to achieve the above-described control sequence will be apparent to those skilled in the art. Also, as shown in the drawings, the apparatus is provided with suitable vent lines and overflow lines and safety devices in accordance with standard engineering practice as will be apparent to those skilled in the art.

The preferred embodiment of the process of the invention will now be described.

The preparatory steps for the practice of the process of sequential solvent extraction in accordance with the invention include (1) filling the reservoirs 10, 12 and 14 with the solvents n-pentane, benzene and pyridine, respectively, which is in an arrangement of increasing polarity, and (2) preparing the sample to be analyzed and delivering the same to the filter chamber 22 of filter 16. In step (1) above it is noted that the solvents are arranged in increasing polarity so that the weakest solvent, n-pentane, can be used first, the next strongest solvent, benzene, second, and the strongest solvent pyridine last. In this mode of operation, the order of usage is important so as to provide for the extraction of organic material into the solvent that is most similar to the chemical properties of the extracting solvent. Obviously, if pyridine were used first, for example, it would dissolve all of the components of the sample that should be dissolved in the weaker solvents.

In accordance with step (2) the inlet plate 19 at the top of filter 16 is removed and a 142 mm. area filter element 24 with a 5 micron size exclusion limit is installed, after which the parts are assembled together in the arrangement best shown in FIGS. 1 and 3 and made to fit tightly so as to avoid any possible leakage.

Separately, a sample of coal-derived material from a coal liquefaction process stream is prepared by mixing 2-5 grams thereof with the least polar solvent n-pentane in this case; to provide approximately 150-200 ml. The sample is delivered into filter 16 through fill tube 28. In order to perform this step, flexible tube 44 which is normally secured to fill tube 28 by conventional clamps, is removed temporarily providing an opening for the delivery of the sample.

At the same time, sonicator 50 is mounted on filter 16 as shown in FIGS. 2 and 3 with probe 52 extending into filter chamber 22. The start button of the microprocessor control means is now closed and the apparatus shown in FIG. 1 to 4 will function automatically to perform the sequential solvent separation of the constituents of the coal liquefaction process stream sample. Briefly, this automated operation involves the sequential opening and closing of the pneumated-operated valves 31, 33, 35, 42, 66, 81, 83 and 85 in accordance with a timed sequence as well as in response to certain conditions of the solvent streams as will be explained hereafter.

The first step in the sequence is to open valve 31 with all the other valves remaining closed. This allows the n-pentane to flow by gravity from reservoir 10 through flow lines 11 and 32 into the metering receiver 46. This condition is maintained until receiver 46 is filled with a 1 liter solvent charge.

Valve 31 is then closed and valve 42 is opened allowing the n-pentane to flow by gravity from receiver 46 through lines 38 and 44 and the fill tube 28 into the filter chamber 22 to provide an arrangement as shown in FIG. 3 with the solvent located on top of the coal sample. When this is accomplished valve 42 is closed.

Next, sonicator 50 is turned on for a predetermined period of time to agitate the solution of coal-derived material and n-pentane. The length of time is determined by experience and can vary from one minute to one hour. Also, the duration can vary with different levels of power that are applied to sonicator 50. As was stated above, the extracting utilizing ultrasonic energy as opposed to filtration results in a substantial reduction of time as compared to conventional filtration procedures. Sonicator 50 is then shut off in preparation for the next step in the process.

Valve 66 is opened allowing nitrogen gas at a predetermined pressure (such as, for example, 10 psi) to flow from supply line 58 through lines 62 and 64 into the top of the filter chamber 22. At the same time, valve 81 is opened providing flow communication to receiver 70 for the n-pentane. The nitrogen under pressure then forces the n-pentane and the materials from the sample dissolved therein through filter element 24 and outlet 30, line 76, line 80 and line 71 into receiver 70. This flow continues until the n-pentane passes through filter 24 to empty from filter chamber 22. While the solvent is flowing through line 76 during the above-described filtration operation, detector 88 senses the condition of the solvent flowing from filter 16 to receiver 70. If detector 88 determines that this solvent stream contains dissolved material from the sample, it will issue a signal to the microprocessor control to repeat the above-described steps for another complete cycle. On the other hand, if detector 88 senses that the solvent stream contains no dissolved material from the sample, i.e., it is pure n-pentane (this would occur when the detector 88 has a response which matches feedback loop of the detector), then the desired level of extraction has been reached and detector 88 issues a signal instructing the microprocessor control to sequence to the next solvent extraction step.

In the next solvent extraction step benzene is used to extract material from the sample and the procedure is identical to that described with respect to the n-pentane procedure with the exception that valve 33 is opened at the time when valve 31 was opened in the n-pentane procedures. When detector 88 senses the endpoint of the benzene solvent extraction procedures, it signals the microprocessor control to sequence to the next step, which is the pyridine solvent extraction step. Again, the procedure is identical to that of the n-pentane solvent extraction procedure with the exception that valve 35 is opened at the time when valve 31 was opened in the n-pentane procedure.

At the end of the pyridine solvent extraction step, the control means provides a signal that the automated solvent extraction operations have been completed. At this stage, the receivers 70, 72 and 74 contain the materials extracted from the sample by the solvents n-pentane, benzene, and pyridine, respectively. Also, remaining on filter element 24 is a residue of those materials that have not dissolved in the solvents and filter 16 is opened to permit removal of filter element 24 and the residue. The solvent contents in receivers 70, 72 and 74 and the residue on filter element 24 are analyzed to enable the user to evaluate the condition of the sample, which information can be utilized to vary the process from which the sample was taken in accordance with conventional analytical methods and techniques.

The entire process of the invention can be performed in less than four man-hours.

It is to be noted that various changes may be made in the apparatus and process of the invention without departing from the scope thereof. For example, various types of endpoint detectors in place of the ultraviolet detector 88 may be utilized. For example, a visible spectrophotometer may be used in which one frequency is detected and used as a reference. Also, a means for detecting a refractive index may be used. Finally, if sufficient experience indicates it is possible, the endpoint of solvent extraction may simply be determined by a set number of filtration cycles, after which the apparatus is sequenced to the next solvent.

EXAMPLES

EXAMPLE 1

This example illustrates the treatment of a solid Solvent Refined Coal (SRC) sample in a process of the invention to define sample size (gram) and quantity of hexane to extract the oils. Kentucky #9 coal, Fies Mine, was used at the Wilsonville, Ala., pilot plant to produce the solid SRC sample No. 67248, Run 220B. Operating parameters and other information are reported in "Solvent Refined Coal (SRC) I Operation of Solvent Refined Coal at Wilsonville, Ala., Monthly Technical Progress for November 1980." A 2.0268 gram sample of solid SRC was ground to 100 mesh size and slurried with hexane prior to filling chamber 22 with the mixture. The sample mixture was extracted with hexane in solvent reservoirs 10, 12, and 14. It was determined that the 2 gram sample required six one liter washes of hexane to complete the extraction and yield 12.7 weight % oils.

EXAMPLE 2

This example illustrates the treatment of a solid SRC in accordance with the process of the invention to perform extraction by n-pentane, a weaker solvent than hexane. SRC sample (No. 67248) was weighed to 2.0088 grams and extracted in the invention with n-pentane in reservoirs 10, 12, and 14. It was determined that 9.2 weight % oils were extracted with six liters of n-pentane.

EXAMPLE 3

This example illustrates the treatment of solid SRC in accordance with the invention to perform extraction by benzene, a stronger solvent than hexane (example 1) or n-pentane (example 2). SRC sample (No. 67248) was weighed to 2.0110 grams and extracted in the invention with benzene as solvent in reservoirs 10, 12 and 14. The extraction required 6–8 liters of benzene for a yield of 75.8 weight % of oils and asphaltenes combined.

EXAMPLE 4

A reproducibility study was made using the process of the invention with n-pentane and another sample. This sample was a total liquid product from Kentucky #9 coal generated in a bench-scale coal liquefaction unit under typical SRC-I liquefaction conditions, i.e., 840° F., 2000 psig and 40 minutes residence time. This sample was analyzed twice on separate days by the same technician. The results are listed in Table 1.

TABLE 1

| Run Date | Sample wt. (grams) | % Oil | % Recovery |
| --- | --- | --- | --- |
| 8/17/82 | 1.9065 | 55.4 | 99.9 |
| 8/18/82 | 1.9498 | 53.9 | 101.1 |

EXAMPLE 5

To test the endpoint detection device, i.e., determine when extraction by a solvent is complete, a visible spectrophotometer was used at 550 nm setpoint. As the visible spectrophotometer was used in the transmittance mode, the higher the value % Transmittance (T), the closer is an endpoint. It was determined that six washes of n-pentane gave sufficient extraction of the sample used in example 4, above, to complete the cycle. The values of % T are given in Table 2. The results indicated that a % T of 75, after six washes, was a proper setpoint for termination of n-pentane extraction.

TABLE 2

| Drain | % T |
| --- | --- |
| 1 | 14.9 |
| 2 | 55.5 |
| 3 | 57.4 |
| 4 | 71.7 |
| 5 | 78.6 |
| 6 | 73.5 |
| 7 | 75.1 |

What is claimed is:

1. An automated process for performing sequential solvent extraction of a product having more than one component comprising the steps of:
    (a) delivering a metered amount of a first virgin solvent or solvent mixture into a filter chamber of a filter containing the product to be analyzed, said filter possessing pore sizes of from 0.5 to 10 microns,
    (b) agitating the solution of the product and said first solvent or solvent mixture for a predetermined period of time by means of a sonicator,
    (c) introducing an inert gas under pressure into said filter chamber to cause said first solvent or solvent mixture to pass through the filter and delivering said first solvent or solvent mixture that has passed through the filter into a receiver therefor,
    (d) repeating said steps (a)–(c) with said first solvent or solvent mixture until a desired level of extraction has been achieved,
    (e) after the desired level of extraction is achieved, repeating steps (a)–(c) for a second virgin solvent or solvent mixture,
    (f) after a desired level of extraction has been achieved for said second solvent or solvent mixture, repeating the above steps (a)–(c) for a third virgin solvent or solvent mixture, and
    (g) collecting streams of each of said solvent or solvent mixtures passing through said filter in individual receivers.

2. A process according to claim 1 wherein the product is prepared by mixing it with a quantity of the least polar of said three solvents or solvent mixtures.

3. A process according to claim 1 wherein the solvents or solvent mixtures are delivered to the filter chamber under gravity feed conditions.

4. A process according to claim 1 wherein said inert gas is nitrogen.

5. A process according to claim 1 wherein the level of extraction is determined by use of a spectrophotometric response.

6. A process according to claim 1 wherein the level of solvent extraction is determined by the use of a visible spectrophotometer.

7. A process according to claim 1 wherein the level of solvent extraction is determined by the measurement of refractive index.

8. A process according to claim 1 wherein the level of solvent extraction is determined by a predetermined number of solvent extraction cycles.

9. An automated process for performing sequential solvent extraction of an animal, vegetable or mineral matter by at least three virgin solvents or solvent mixtures of different solubility factors with respect to said animal, vegetable or mineral matter which comprises the steps of:
    (a) delivering a metered amount of the weakest of said virgin solvents or solvent mixtures into a filter chamber having a fine filter therein possessing pore sizes of from 0.5 to 10 microns and containing said animal, vegetable or mineral matter which is to be solvent extracted;
    (b) agitating by an ultrasonic agitation means said contents of said filter chamber for a predetermined period of time;
    (c) introducing an inert gas under pressure into said filter chamber to cause the solution therein to pass through said fine filter and delivering a first captured solvent or solvent mixture downstream of said fine filter into a receiver;
    (d) continuously and sequentially repeating steps (a), (b) and (c) until a desired level of extraction is indicated by a detector means located downstream of said fine filter;
    (e) delivering a metered amount of the next weakest virgin solvent or solvent mixture into said filter chamber having said fine filter therein possessing pore sizes of from 0.5 to 10 microns and containing said animal, vegetable or mineral matter that has been previously solvent extracted by said weakest virgin solvent or solvent mixture;
    (f) agitating by said ultrasonic agitation means said contents of said filter chamber in step (e) for a predetermined period of time;

(g) introducing an inert gas under pressure into said filter chamber of step (f) and delivering a second captured solvent or solvent mixture downstream of said fine filter into a receiver;

(h) continuously and sequentially repeating steps (e), (f) and (g) until said desired level of extraction is indicated by said detector means located downstream of said fine filter;

(i) delivering a metered amount of the least weakest of said virgin solvents or solvent mixtures into said filter chamber having said fine filter therein possessing pore sizes of from 0.5 to 10 microns and containing said animal, vegetable or mineral matter that has previously been solvent extracted by said weakest and next-to-weakest virgin solvent or solvent mixture;

(j) agitating by said ultrasonic agitation means said contents of said filter chamber in step (i) for a predetermined period of time;

(k) introducing an inert gas under pressure into said filter chamber of step (j) and delivering a third captured solvent or solvent mixture downstream of said fine filter into a receiver; and (l) continuously and sequentially repeating steps (i), (j) and (k) until said desired level of extraction is indicated by said detector means located downstream of said fine filter.

10. The process of claim 9 wherein the solvents or solvent mixtures comprise normal pentane for the weakest solvent, benzene for the next weakest solvent and pyridine for the least weakest solvent.

11. The process of claim 10 wherein the animal, vegetable or mineral matter comprises fossil fuels, shale oil derivatives or solvent refined coal products.

12. The process of claim 9 wherein said animal, vegetable or mineral matter is selected from the group consisting of leaves, bark, roots, stems, wood, seeds, nuts, petals, and fruit.

13. The process of claim 12 wherein said matter is present in a fresh, dried or chipped state.

14. The process of claim 9 wherein the animal, vegetable or mineral matter comprises animal cell tissue, bacteria or tissue cultures.

15. The process of claim 9 wherein more than three virgin solvents or solvent mixtures are used to solvent extract said animal, vegetable or mineral matter in continuous and sequential separation steps until said extraction is detected as complete downstream of said fine filter.

16. The process of claim 9 wherein said ultrasonic agitation means comprises a sonificator.

17. The process of claim 9 wherein said inert gas comprises nitrogen, helium, or argon.

18. The process of claim 17 wherein said detector means is located in a conduit connecting said filter chamber with each of said receivers.

19. The process of claim 9 wherein said detector means comprises an ultraviolet detector or an infrared detector.

20. The process of claim 9 wherein said receiver in steps (c), (g) and (k) is a unitary vessel.

21. The process of claim 9 wherein said receivers of steps (c), (g) and (k) are unitary entities receiving the respective captured solvent or solvent mixtures from the inert gas purge steps of steps (c), (g) and (k).

* * * * *